United States Patent [19]

Berg

[11] Patent Number: 4,832,016

[45] Date of Patent: May 23, 1989

[54] REMOTELY CONTROLLED ACTUATOR FOR A RESUSCITATOR

[76] Inventor: Kent Berg, 9 Bubbling Creek Dr., Travelers Rest, S.C. 29690

[21] Appl. No.: 166,413

[22] Filed: Mar. 10, 1988

[51] Int. Cl.[4] ............................ A62B 9/02; A62B 9/04
[52] U.S. Cl. ........................... 128/205.24; 128/204.18; 128/205.18; 128/205.17
[58] Field of Search ...................... 128/202.27, 203.25, 128/204.18, 205.11, 207.16, 28, 30, 30.2, 200.27, 200.28, 200.29, 203.11, 205.18, 205.13, 205.23, 205.24, 203.12, 203.14, 203.24, 207.12, 207.14

[56] References Cited

U.S. PATENT DOCUMENTS

| | | | |
|---|---|---|---|
| 3,252,457 | 5/1966 | Monaco et al. | 128/203.11 |
| 3,333,581 | 8/1967 | Robinson et al. | 128/30.2 |
| 3,795,257 | 3/1974 | Fabish et al. | 128/204.26 |
| 4,202,330 | 5/1980 | Jariabka | 128/204.18 |
| 4,349,015 | 9/1982 | Alferness | 128/205.17 |
| 4,579,114 | 4/1986 | Gray et al. | 128/203.11 |
| 4,620,538 | 11/1986 | Koegel et al. | 128/201.23 |
| 4,664,098 | 5/1987 | Woudenberg et al. | 128/53 |
| 4,676,232 | 6/1987 | Olsson et al. | 128/30.2 |

FOREIGN PATENT DOCUMENTS

| | | | |
|---|---|---|---|
| 0014615 | 8/1901 | Sweden | 128/205.18 |
| 0399657 | 3/1966 | Switzerland | 128/205.18 |

Primary Examiner—Edgar S. Burr
Assistant Examiner—Kimberly L. Asher
Attorney, Agent, or Firm—Bailey & Hardaway

[57] ABSTRACT

A remotely controlled actuator for a resuscitator to be used in conjunction with a demand valve assembly regulating breathing or resuscitation equipment.

4 Claims, 2 Drawing Sheets

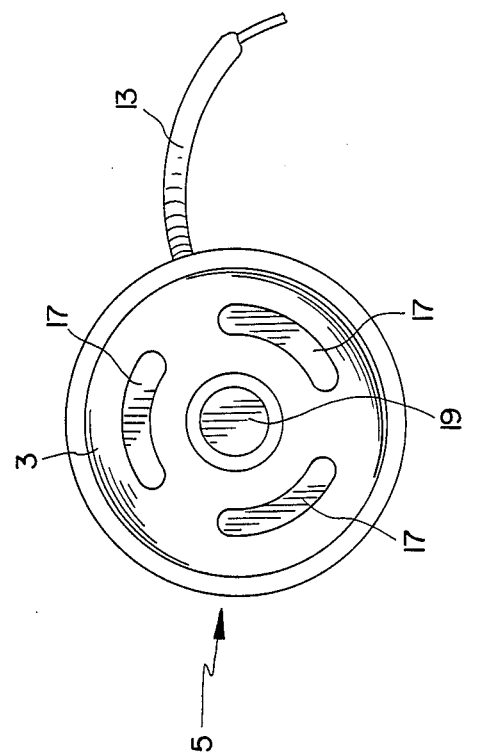

REMOTELY CONTROLLED ACTUATOR FOR A RESUSCITATOR

BACKGROUND OF THE INVENTION

This invention relates generally to the art of resuscitation equipment and more particularly to an apparatus which actuates a demand valve assembly used to regulate breathing or resuscitation equipment.

In emergency medical situations, the condition of a patient frequently requires that rescuers perform several life-saving procedures concurrently, including cardiopulmonary resuscitation (CPR), the control of hemorrhaging, administration of drug therapy, interpretation of EKG, etc. Performance of each individaul task must be properly and efficiently executed in order to provide timely benefit to the patient. There are severe limitations, however, which must be overcome in order to render optimal service.

If a patient requires cardiopulmonary resuscitation, rescuers administer this procedure at once. Effective CPR performed either manually or with mechanical assistance includes both chest compressions to stimulate the patient's heart and ventilation of the patient's lungs. The timing and coordination of the chest compressions with the ventilation of the lungs is critical, and efficient performance is extremely difficult, even by two trained medical technicians, each attending to a different function.

Efficiency is promoted, however, by use of automated CPR apparatus or resuscitators. Use of a resuscitator also typically enables CPR to be performed by a single rescuer, freeing a second rescuer to effect other life-saving measures. Such apparatus may include a means, such as a plunger, for compressing the patient's chest, an airway device comprising of an endotracheal tube, a tracheotomy tube or an air hose and associated mask, or a combination of both.

The prior art provides a variety of devices for mechanically assisting CPR procedures performed by a single rescuer. These devices, comprehensive in scope, include U.S. Pat. No. 4,664,098 to Woudenberg, et al., disclosing a cardiopulmonary resuscitator which performs mechanical CPR while restraining the patient's chest against lateral displacement during the operation of a plunger mechanism.

In U.S. Pat. No. 4,349,015 to Alferness, a manually-actuable CPR apparatus is described, including a bellows on a patient's chest which, when manually compressed, contributes to the increase of the patient's intrathoracic pressure.

A pulmonary resuscitator with electrical control system, described in U. S. Pat. No. 3,333,581 to Robinson, et al., provides for the resuscitation of patients exhibiting breathing difficulties, the operational mode of which may be electrically regulated in accordance with presented needs.

Other related devices are disclosed in U.S. Pat. No. 4,676,232 to Olsson, et. al., and in U.S. Pat. No. 4,620,538 to Koegel, et al.

Additionally, a particular valve assembly is described in U.S. Pat. No. 3,795,257 to Fabish, et al., to be used in conjunction with breathing or resuscitation equipment.

Whereas the aforementioned resuscitators allow CPR administration by a single rescuer and are perhaps more efficient than non-mechanical means in reproducing cardiac and pulmonary functions. They are bulky, cumbersome and expensive. In addition, in the case of a pulmonary resuscitator, its mechanical operation supersedes the patient's own attempts at breathing as well as the need to hyperventilate the patient following transtracheal drug therapy or suctioning. Further, even under optimal conditions, the use of the device challenges the rescuer to time chest compressions for perfect integration with programmed ventilations. Even though a single rescuer can adequately perform CPR with the assistance of a resuscitator, the factors of bulk, size, expense and being inappropriate at well-defined times do not allow resuscitators to be viable options for most emergency services.

SUMMARY OF THE INVENTION

It is thus an object of this invention to provide a novel apparatus to be utilized in conjunction with a demand valve assembly used to regulate breathing or resuscitation equipment.

It is a further object of this invention to provide a novel apparatus which actuates the demand valve assembly by remote control.

It is still a further obejct of this invention to provide a novel apparatus for use by a single rescuer administering comprehensive CPR.

It is a more particular object of this invention to provide a novel apparatus which allows for numerous ventilation rates and compression-to-respiration ratios during the administration of CPR.

These, as well as other objects, are accomplished by a remotely controlled actuator for a resuscitator to be used in conjunction with a demand valve assembly regulating breathing or resuscitation equipment comprising a housing, defining an open-ended chamber, tapered at one end and having a threaded connection at the other end, a cap with a threaded connection for purposes of connecting with the housing, a finger-fitted injector mechanism including a slidable wire, a hollow tube connecting the cap with the injector mechanism and defining a passage means for the slidable wire, arcuate slots formed about the tapered end of the housing and a notch formed at the other end of the housing.

BRIEF DESCRIPTION OF THE DRAWINGS

FIG. 3 of the drawings is an end perspective view illustrating the arcuate slots on the tapered end of the housing and the opening for the outlet passage of the demand valve assembly.

DETAILED DESCRIPTION OF THE DRAWINGS

Figure 1:
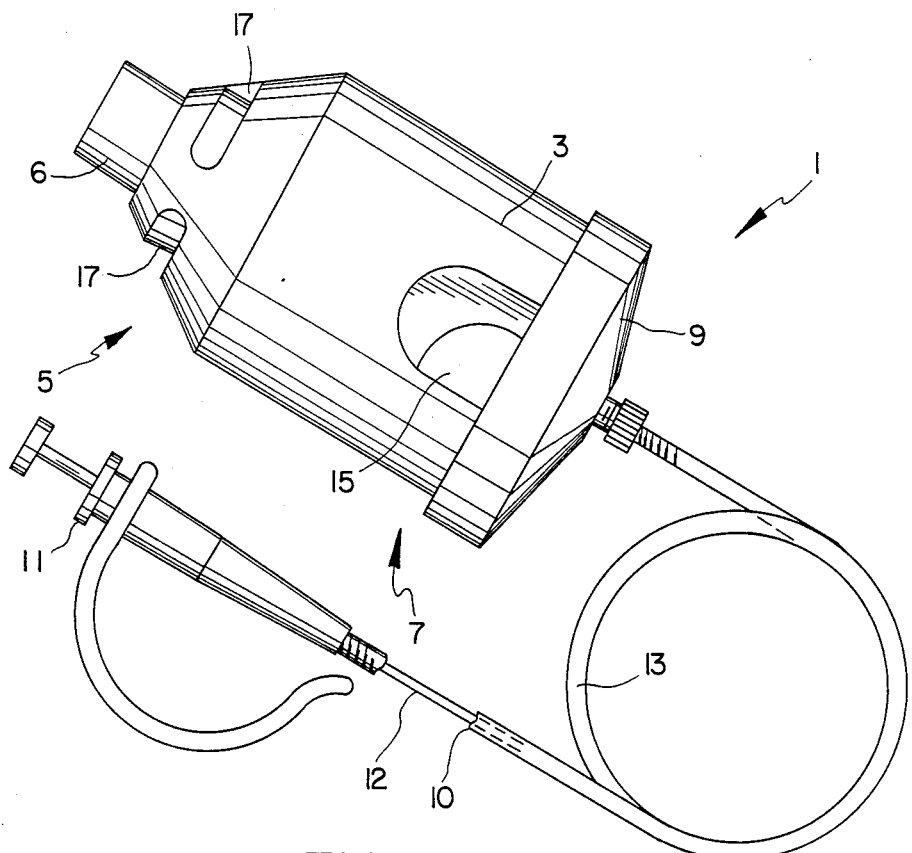
FIG. 1 of the drawings is a side perspective view of the apparatus in accordance with this invention showing the cap screwed onto the housing in operating position.

The apparatus of the instant invention is intended to be used in conjunction with a demand valve assembly which regulates, by activation of its button assembly, a breathing device or pulmonary resuscitator. Accordingly, the demand valve assembly complete with button assembly disclosed in U.S. Pat. No. 3,795,257 to Fabish, et al., is hereby incorporated by reference.

The purpose of the demand valve assembly is to control the availability of pressurized gas to the patient, supplying it upon demand. The demand valve assembly operates either by manual actuation of its button assembly or as a result of the patient beginning to breathe normally. It is currently in wide-spread use by rescue teams of paramedics or other tranined medical technicians as an invaluable part of the mechanical assist to the CPR effort.

Use of the demand valve assembly poses certain restrictions on the rescue team, however, including the full attention of one rescuer who must hold, monitor and operate it. Not only is it operated manually in the event the patient is not breathing normally, but it must be hand-held in a neutral position so that the associated tube is not displaced, causing airway compromise and possible pharangeal damage. This is of particular importance at such time as the patient is moved to a new location.

In requiring one rescuer to hold the device, early performance of life-saving procedures other than CPR may be jeopardized. Since most rescue teams are staffed by only two (2) rescuers and if CPR is required by the patient, advanced care must necessarily by delayed until additional help arrives, compromising the patient's chances of survival.

A further consideration is that of limited space in which to administer to the patient. If the patient happens to be in a particularly confined area, e.g., a factory aisle, bathroom, narrow hallway, between pieces of machinery or aboard an aircraft, the efficiency of rescuer performance becomes even more critical since additional workers could not reach the patient even if they do arrive in time.

Thus, the medical emergency would greatly benefit from a device which allows coordination of the induced pulmonary and cardiac functions by a single rescuer, which is also convenient to use and financially obtainable by most medical services.

In accordance with this invention, there is provided an apparatus to be used in conjunction with the demand valve assembly including button assembly incorporated herein by reference. The apparatus is light weight, easily manageable, and inexpensive to obtain. Its function is to actuate the demand valve assembly by making contact with the button assembly, and it is fitted to the hand of the rescuer administering chest compressions. This arrangement enables a single rescuer to remotely control the demand valve assembly so that ventilations to the patient are coordinated appropriately with chest compressions by the rescuer. When conditions dictate the necessity to adjust the established compression-to-respiration ratio, the required change is easily performed and the new pattern readily maintained.

Effective CPR procedures can be carried out even in crowded quarters which prohibit more than one rescuer alongside the patient, and advanced life saving measures can be administered by a second rescuer concurrently with CPR. These, as well as other advantages, will be apparent from the following description and reference to the figures of drawings.

FIG. 1 of the drawings illustrates the actuator 1 including housing 3 having distal end 7 and tapered proximal end 5 terminating in extension 6. The actuator further includes cap 9 secured at distal end 7 of housing 3, a conventional finger-fitted injector mechanism 11 including wire 12 having terminal end 14, tube 13 connecting injector mechanism 11 with cap 9 and defining passage means 10, notch 15 formed at distal end 7 of housing 3 and arcuate slots 17 formed about tapered proximal end 5 of housing 3.

Figure 2:
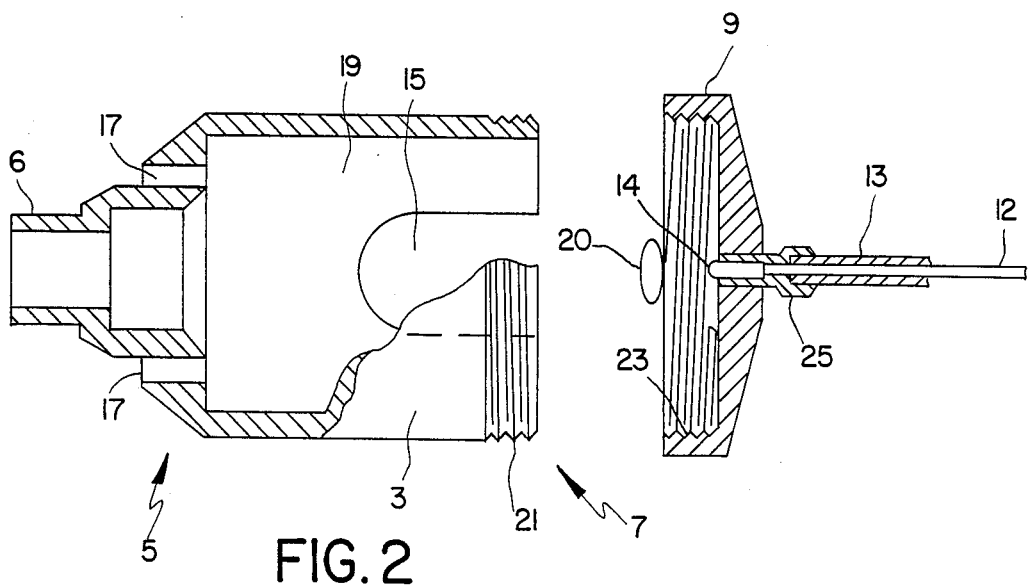
FIG. 2 of the drawings is a longitudinal sectional view of the housing of the apparatus in accordance with this invention.

In FIG. 2 of the drawings, chamber 19 is shown for receiving the demand valve assembly in hand-in-glove fashion, allowing the button assembly to be located at 20 of the demand valve assembly (not shown) to be positioned centrally at distal end 7 of housing 3, the outlet passage of the demand valve assembly (not shown) to fit with close tolerances within that part of chamber 19 defined by extension 6 of tapered proximal end 5 of housing 3, and further allowing the inlet passage of the demand valve assembly (not shown) to be slidably received by notch 15 at distal end 7 of housing 3. The arcuate slots of the demand valve assembly (not shown) then align with arcuate slots 17 about tapered proximal end 5 of housing 3. Threaded connection 21 at distal end 7 of housing 3 is also shown in FIG. 2, as is threaded connection 23 of cap 9, for securing cap 9 to housing 3. Passage means 25 defined by cap 9 houses terminal end 14 of wire 12.

In FIG. 3 of the drawings, arcuate slots 17 are shown arranged about tapered proximal end 5 of housing 3.

The process of this invention is carried out by inserting the demand valve assembly (not shown) into chamber 19 of housing 3 such that the button assembly of the demand valve assembly is positioned centrally at distal end 7 of housing 3, the outlet passage of the demand valve assembly fits snugly through the tapered end 5 of housing 3, the inlet passage is slidably received by notch 15 of housing 3 and the arcuate slots of the demand valve assembly align properly with arcuate slots 17 of housing 3. Cap 9 is secured onto the distal end 7 of housing 3. The rescuer then positions his hand within the finger-fitted injector mechanism 11. When the mechanism 11 is manually actuated, wire 12 is forced along passage means 10 of connecting tube 13 such that terminal end 14 of wire 12 moves through passage means 25 defined by cap 9 to make direct contact with the button assembly (not shown) of the demand valve assembly. This process causes the operation of the demand valve assembly, which ultimately allows pressurized air to reach the patient.

In the event the patient resumes normal breathing patterns, the rescuer would simply cease the actuation of the demand valve assembly. Because of the finger-fitted mechanism of the actuator, this is easily effected.

It is thus seen that the remotely controlled actuator for a demand valve assembly described herein is a novel and effective means for allowing a single rescuer to administer comprehensive CPR. Further, the instant invention is particularly noteworthy in that it enables the attending rescuer to readily effect whatever compression-to-respiration ratio is required and to alter it as conditions change. As variations of the instant invention will be apparent to one of skill in the art from a reading of the above specifications, such variations are within the spirit and scope of this invention as defined by the following appended claims:

That which is claimed:

1. A remotely controlled actuator for a resuscitator to be used in conjunction with a demand valve assembly regulating breathing or resuscitation equipment comprising:

a housing defining an open-ended chamber and having a proximal end and a distal end, said housing tapered at said proximal end and having a threaded connection at said distal end;

a cap with a threaded connection for accepting and connecting with said distal end of said housing;

a finger-fitted injector mechanism including a slidable wire;

a hollow tube connecting said cap with said injector mechanism, and tube defining a passage means for said slidable wire;

arcuate slots formed about said tapered proximal end of said housing; and, a notch formed at said distal end of said housing.

2. The remotely controlled actuator for a resuscitator to be utilized in conjunction with a demand valve assembly including a button assembly used with breathing or resuscitation equipment in accordance with claim 1 wherein said actuator encompasses said demand valve assembly in hand-in-glove fashion allowing the button assembly of said demand valve assembly to be positioned centrally at said distal end of said housing, the outlet passage of said demand valve assembly to fit with close tolerances through said tapered proximal end of said housing, the inlet passage of said demand valve assembly to be slidably received by said notch at said distal end of said housing and the arcuate slots of said demand valve assembly to align with said arcuate slots of said housing.

3. The remote actuator for a resuscitator to be utilized in conjunction with a demand valve assembly in accordance with claim 1 wherein said cap defines a passage means through its central portion directly opposite the button assembly of said demand valve assembly, said passage means allowing access to said button assembly.

4. A process of actuating a resuscitator to be used in conjunction with a demand valve assembly, which assembly includes a button assembly, an outlet passage, an inlet passage and arcuate slots, comprising the steps of:

providng an actuator comprising a housing defining an open-ended chamber and having a proximal end and a distal end;

a cap with threaded connection;

a finger-fitted injector mechanism including a slidable wire;

a hollow tube connecting said cap with said injector mechanism, said tube defining a passage means for said slidable wire;

arcuate slots formed about said proximal end of said housing;

a notch formed at said distal end of said housing;

inserting said demand valve assembly into said chamber of the housing of the actuator whereby said button assembly of said demand valve assembly is positioned centrally at the distal end of said housing, said outlet passage of said demand valve assembly fits through said tapered proximal end of said housing, said inlet passage of said demand valve assembly is slidably received by said notch at said distal end of said housing and said arcuate slots of said demand valve assembly are properly aligned with said arcuate slots of said housing;

securing said cap onto said distal end of said housing, positioning said passage means of said cap directly opposite said button assembly of said demand valve assembly;

positioning said finger-fitted injector mechanism onto a rescuer's hand; and, activating said mechanism manually, forcing said slidable wire through said passage means to contact said button assembly of said demand valve assembly, causing the operation of said demand valve assembly.

* * * * *